United States Patent [19]

Schwanbom et al.

[11] 4,313,436
[45] Feb. 2, 1982

[54] FRESH GAS DEVICE WITH MIXER FOR MEDICAL AND RESPIRATION APPARATUS

[75] Inventors: Erik Schwanbom; Karl Hickmann, both of Lübeck, Fed. Rep. of Germany

[73] Assignee: Dragerwerk Aktiengesellschaft, Fed. Rep. of Germany

[21] Appl. No.: 198,818

[22] Filed: Oct. 20, 1980

[30] Foreign Application Priority Data

Nov. 10, 1979 [DE] Fed. Rep. of Germany ....... 2945575

[51] Int. Cl.³ ............................................ A61M 16/00
[52] U.S. Cl. .......................... 128/203.12; 128/200.19; 128/205.24; 137/110
[58] Field of Search ...................... 128/200.19, 203.12, 128/203.14, 203.16, 202.22, 203.25, 204.21, 204.24, 205.24, 205.11; 137/110, 112, 637.1

[56] References Cited

U.S. PATENT DOCUMENTS

| 2,041,863 | 5/1936 | Rhodes | 137/110 |
| 3,351,089 | 11/1967 | Garrahan | 128/205.24 |
| 3,807,425 | 4/1974 | Boirum et al. | 137/110 |
| 3,896,837 | 7/1975 | Rohling | 137/110 |
| 3,957,044 | 5/1976 | Fletcher et al. | 137/110 |
| 4,195,667 | 4/1980 | Moore et al. | 137/637.1 |
| 4,215,409 | 7/1980 | Strowe | 128/203.14 |

*Primary Examiner*—Henry J. Recla
*Attorney, Agent, or Firm*—McGlew and Tuttle

[57] ABSTRACT

An improved fresh gas device includes a gas mixer connected to a source of oxygen and to a source of at least one other gas for mixing oxygen to form a gas mixture to be supplied to a patient. A line bypasses the mixer and is provided with a switch for initiating pressure pulses in the bypass line and a pneumatically operated valve is provided downstream of the mixer and is controllable responsive to the pressure in the bypass line.

5 Claims, 1 Drawing Figure

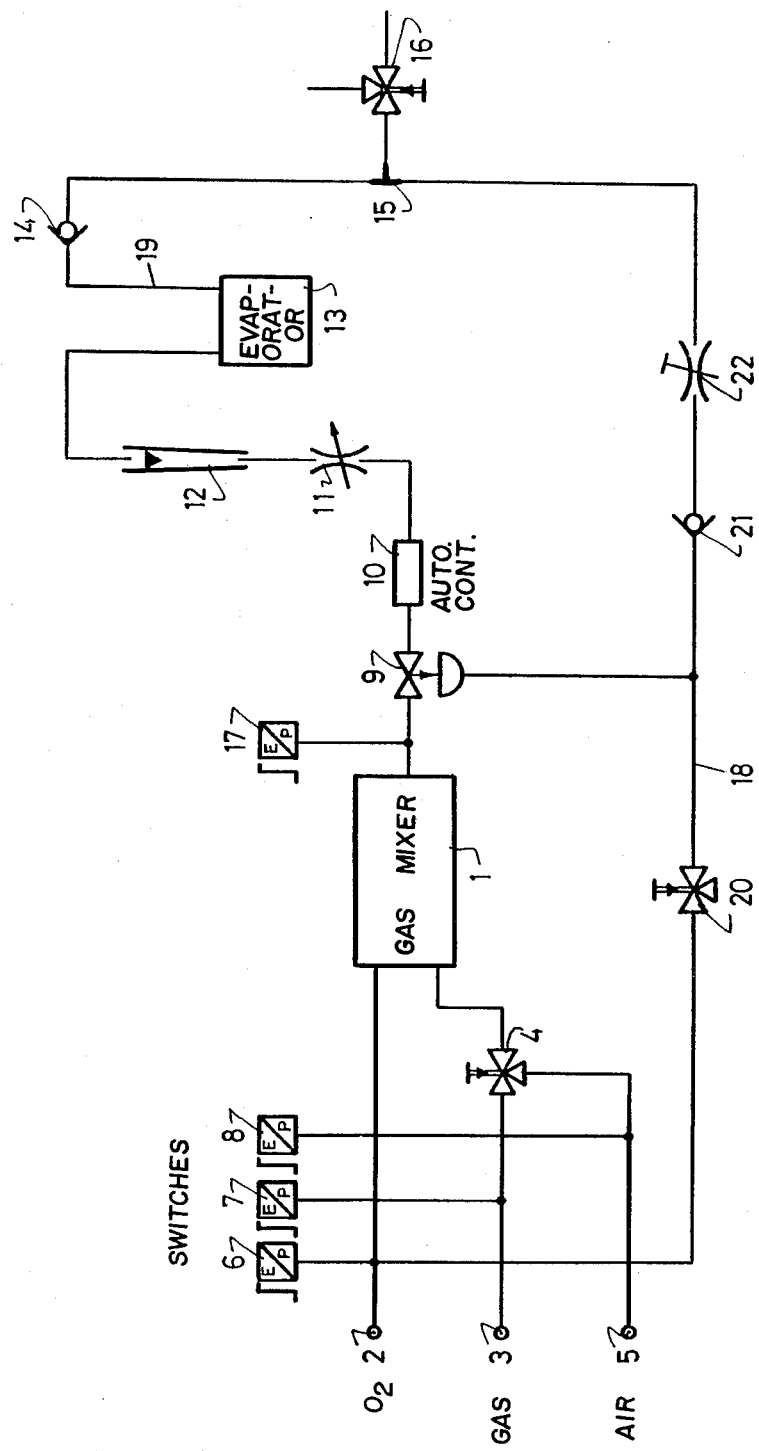

FRESH GAS DEVICE WITH MIXER FOR MEDICAL AND RESPIRATION APPARATUS

FIELD AND BACKGROUND OF THE INVENTION

This invention relates to respiratory apparatus in general and, in particular, to a new and useful fresh gas device with a mixer for medical and respiration apparatus.

For the safety of patients hooked up to the respirators, either for anaesthesia or resuscitation, it must be possible to supply them with pure oxygen at any time. The need for pure oxygen can arise spontaneously due to irregularities in the circulatory conditions of the patient or due to incorrectly selected dosages of fresh gas.

West German published patent application No. DE-OS No. 22 16 222 discloses a portable apparatus for anaesthesia and respiratory resuscitation, which can be set up as a wall-mounted unit. The apparatus consists of a first part where the fresh gas, for supplying the second part with the circuits for anaesthesia and respiratory resuscitation, is being purified.

Of particular interest here is the first part, which is assembled from structural units arranged on a baseplate, to which the second part, having various treatment circuits, is connected. It contains one line for oxygen and one line for laughing gas, which lead to a gas mixing block, via an adjustable reagent feeder. For an emergency oxygen feed, there is an additional oxygen line, equipped with a valve, parallel to the other lines attached to the gas mixing block. The gas mixing block, in the direction of the gas flow, is followed by a disengageable evaporator for anaesthesia liquids, which is located upstream of a check valve, openable in the flow direction of the current, and connected to the second part. During the operating condition for anaesthesia, oxygen and laughing gas, properly metered and mixed, flow through the evaporator and there pick up the anaesthetic vapors. The fresh gas thus prepared then flows through the check valve, which prevents flow reversal, via the second part, and towards the patient. During respiratory resuscitation, proper dosages of oxygen bypass the isolated evaporator and flows toward the patient. Additional operating conditions, resulting from combinations of the two foregoing arrangements are possible.

An emergency feed supply of oxygen may be made directly through the remaining line circuit, without the reagent feeder. Disadvantages occur during this operating condition because of continuously flowing gases, in that an ill-defined oxygen supply occurs, and in that, it is necessary to turn off the evaporator. Precise oxygen supply demandes require, in addition, the switching off of the reagent feeder and, accordingly, the stopping of the flow of the laughing gas. Apart from this additional operating step, which requires time and consideration, the dosage must be changed, which then subsequently requires readjustment.

SUMMARY OF THE INVENTION

It is an object of the present invention to provide the possibility of furnishing an immediate supply of pure oxygen to patients on medical and breathing apparatus, with higher dosages and in a simple and safe manner.

It is a further object of the present invention to provide an improved fresh gas device of the type having a gas mixer connected with an inlet line to a source of oxygen and connected to a source of at least one other gas for mixing oxygen and the at least one other gas to form a gas mixture to be supplied to a patient via a patient supply apparatus and an outlet line connected to the mixer for passing the gas mixture to the patient supply apparatus, wherein, the improvement includes a valve located in the outlet line for opening and closing the flow path to the apparatus, a bypass line in a parallel flow path with the mixer connected to the inlet line intermediate the source of oxygen and the mixer and connected to the outlet line intermediate the valve and the apparatus, means for initiating a pressure pulse in the bypass line, and pressure-sensing means operatively connecting the bypass line and the valve for closing the valve responsive to a pressure pulse in the bypass line.

In accordance with a preferred embodiment of the invention, the means for initiating the pressure pulse comprises a pushbutton switch. The valve is preferably a pneumatically operated valve.

In accordance with still further embodiments of the invention, the improved device includes a check valve in the bypass line downstream of the pushbutton switch openable in the flow direction and, as well, a throttle in the bypass line.

An advantageously simple solution is derived from the provision of a bypass line with a pushbutton switch, and the straight through valve, closable by pressure against the pushbutton switch, in the fresh gas line. By depressing the switch, pure oxygen flows from the oxygen source in higher dosages directly, via a tee connection, toward the apparatus section of the respiration device and thus toward the patient. The normal flow path of the fresh gas is, with the through valve closed, immediately blocked off. This does not lead to maladjustments which possible would have to be subsequently corrected. A through valve in the bypass line assures that the oxygen flow passes uninhibited. Through a metering unit, the dosage amount can be adjusted to the patient.

It is a further object of the present invention to provide an improved fresh gas device for supplying a mixture of oxygen and at least one other gas to a patient which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, references is made to the accompanying drawing and descriptive matter in which a preferred embodiment of the invention is illustrated.

BRIEF DESCRIPTION OF THE DRAWING

The sole FIGURE of the drawing is a diagrammatic illustration of an improved fresh gas device, in accordance with the teachings of the present invention.

DESCRIPTION OF THE PREFERRED EMBODIMENT

Turning to the drawing in particular, the invention embodied therein, comprises, a fresh gas device which includes a gas mixer 1, which is supplied with pressurized oxygen from an oxygen connection 2, attached to an oxygen supply (not shown) and with laughing gas from a laughing gas connection 3. Furthermore, air is connected up to the laughing gas connection 3 through a three-way valve 4, with two flow paths, connected to an air connection 5.

A pressure switch 6 for oxygen, a pressure switch 7 for laughing gas and a pressure switch 8 for air, monitor the respective pressures for oxygen, laughing gas and air. The gas mixture produced by the gas mixer 1, hereafter designated "fresh gas", is passed through a pneumatically operated through valve 9 and then reaches an evaporator 13 through an automatic controller 10 and the metering or throttle unit 11, with a flowthrough meter 12.

The fresh gas flow, enriched in the evaporator with anaesthetics, flows through the fresh gas line 19 via a check valve 14, the branch of a tee 15 and then via a through valve 16, to the apparatus section of the respiration device (now shown) and then to the patient. A pressure switch 17, located downstream of the gas mixer and upstream of the pneumatic through valve, monitors the back pressure of the gas mixer 1.

A bypass line 18 connects the oxygen connection 2, via the tee 15, with through valve 16. Bypass line 18 includes a pushbutton switch 20, a check valve 21 and a metering unit or throttle 22.

When pushbutton switch 20 is activated, a pressurized oxygen pulse reaches the pneumatic through valve 9 and closes it. This interrupts the fresh gas flow through the evaporator 13 to the apparatus section. The pressurized oxygen pulse continues via the check valve 21 and throttle 22, the tee 15 and the through valve 16 to the apparatus section. The check valve 14 prevents a pressure build-up at the evaporator 13 and at the outflow side of the pneumatic through valve 9.

When pushbutton switch 20 is not activated, the control side of the pneumatic through valve 9 is relieved of any load. It opens and again releases the fresh fas flow, adjusted through dosage unit 11.

Instead of the oxygen/laughing gas mixture, oxygen can also be mixed with air. For this purpose, the three-two way switch 4 is fed with air. After corresponding activation of the three-two way switch 4, air, instead of laughing gas, flows to gas mixer 1. Gas mixer 1 is equipped so that during a stoppage of one of the supply gases, the mixer outflow is automatically blocked and so that pressure switch 17 triggers a warning signal.

While a specific embodiment of the invention has been shown and described in detail to illustrate the application of the principles of the invention, it will be understood that the invention may be embodied otherwise without departing from such principles.

What is claimed is:

1. An improved fresh gas device of the type comprising a gas mixer having a first inlet line adapted to be connected to a source of oxygen and a second inlet line adapted to be connected to a source of at least one other gas for mixing oxygen and that at least one other gas to form a gas mixture to be supplied to a patient via a patient supply apparatus and said gas mixer having an outlet line adapted to be connected to the patient supply apparatus for passing the gas mixture thereto, the improvement comprising, valve means located in the outlet line for opening and closing the flow path to the apparatus, a bypass line in a parallel flow path with the mixer connected between the inlet line and the outlet line, means for manually initiating a pressure pulse in the bypass line, and pressure-sensing means operatively connected to said bypass line downstream of said initiating means for sensing said pressure pulse, and said valve means being responsive to said pressure sensing means for closing said inlet line when a pressure pulse is sensed in said bypass line.

2. In an improved fresh gas device, the improvement claimed in claim 1, wherein said means for initiating a pressure pulse comprises a pushbutton switch.

3. In an improved fresh gas device, the improvement claimed in claim 2, further comprising a check valve in said bypass line downstream of said pushbutton switch openable in the flow direction, and a throttle in said bypass line.

4. In an improved fresh gas device, the improvement claimed in claim 1, further comprising a check valve in said bypass line downstream of said means for initiating a pressure pulse openable in the flow direction, and a throttle in said bypass line.

5. In an improved fresh gas device, the improvement claimed in claim 4, wherein said valve means comprises means for pneumatically operating said valve means to open and close the flow path through the outlet line.

* * * * *